United States Patent [19]

Dockner et al.

[11] Patent Number: 4,529,537
[45] Date of Patent: Jul. 16, 1985

[54] LIQUID EPOXY RESIN HARDENERS AND PROCESSES FOR THEIR PREPARATION

[75] Inventors: Toni Dockner, Meckenheim; Anton Frank, Ludwigshafen, both of Fed. Rep. of Germany

[73] Assignee: BASF Aktiengesellschaft, Fed. Rep. of Germany

[21] Appl. No.: 627,983

[22] Filed: Jul. 5, 1984

[30] Foreign Application Priority Data

Jul. 6, 1983 [DE] Fed. Rep. of Germany ........ 33/24339

[51] Int. Cl.$^3$ .................. C09K 3/00; H05B 33/00
[52] U.S. Cl. ................................. 252/182; 548/335; 528/94; 528/117; 528/407
[58] Field of Search ............ 528/94, 117, 107, 361, 528/407; 548/335; 252/182

[56] References Cited

U.S. PATENT DOCUMENTS

| | | | |
|---|---|---|---|
| 2,847,417 | 8/1958 | Erner | 260/309 |
| 3,037,028 | 5/1962 | Green | 260/309 |
| 3,177,223 | 4/1965 | Erner | 260/309 |
| 3,489,695 | 1/1970 | Green | 528/117 |
| 4,069,203 | 1/1978 | Carey et al. | 528/94 |
| 4,417,010 | 11/1983 | Shimp | 528/117 |

FOREIGN PATENT DOCUMENTS 1050679 12/1966 United Kingdom .

OTHER PUBLICATIONS

Hofmann, "Imidazoles and Derivatives", p. 328.

*Primary Examiner*—Earl Nielsen
*Attorney, Agent, or Firm*—Keil & Weinkauf

[57] ABSTRACT

Liquid epoxy resin hardeners are mixtures of 2-ethyl-4-methylimidazole, ethyldimethylimidazole and/or diethylmethylimidazole isomers which can also contain other alkylimidazoles, and can be produced by distillation of the products obtained in the dehydrogenation of 2-ethyl-4-methylimidazoline.

4 Claims, No Drawings

LIQUID EPOXY RESIN HARDENERS AND PROCESSES FOR THEIR PREPARATION

The present invention relates to liquid epoxy resin hardeners based on alkylimidazoles, and processes for their preparation.

The dehydrogenation of Δ2-imidazolines over various catalysts to give the corresponding substituted imidazoles is known and is described in, for example, EP No. 0,000,208, German Laid-Open Applications DOS No. 1,952,991 and Dos No. 2,733,466, German Patent No. 2,106,877, U.S. Pat. Nos. 2,847,417, 3,037,082 and 3,177,223 and U.S.S.R. Pat. No. 201,418.

The use of imidazole compounds, such as 2-ethyl-4-methylimidazole, 2-cyclohexyl-4-methylimidazole and 2-octyl-4-hexylimidazole, as epoxy resin hardeners has been disclosed in German Published Application DAS No. 1,301,135. Although this published application states that 2-ethyl-4-methylimidazole is a particularly preferred liquid imidazole, in fact pure 2-ethyl-4-methylimidazole melts at 45° C. (cf. Hofmann, Imidazoles and Derivatives, page 328) and is a solidified crystalline melt at room temperature.

If 2-ethyl-4-methylimidazole is to be used in liquid form as described in German Published Application DAS No. 1,301,135, the crystals have to be melted and the melt handled at above 40° C.

If pure 2-ethyl-4-methylimidazole is mixed with an equal amount of imidazole or of another alkylimidazole, such as 2-methyl-, 2-isopropyl- or 4-methylimidazole, etc., or even with an equal amount of 1-methylimidazole or the starting material 2-ethyl-4-methylimidazoline, both of which are liquid, the resulting mixtures crystallize after a few days to give either a solid crystalline mass or a slurry of crystals.

It is an object of the present invention to provide an epoxy resin hardener based on alkylimidazoles which is liquid and has a very low viscosity at room temperature, remains liquid even at as low as 0° C. and possesses good curing properties.

We have found that this object is achieved, surprisingly, if the epoxy resin hardener used is a mixture of 2-ethyl-4-methylimidazole, ethyldimethylimidazole and diethylmethylimidazole isomers.

The present invention relates to a liquid epoxy resin hardener which comprises a mixture of the following alkylimidazoles:
(A) from 65 to 95% by weight of 2-ethyl-4-methylimidazole and
(B) from 5 to 35% by weight of one or more compounds from the group consisting of 2-ethyl-4,5-dimethylimidazole and 2,5(4)-diethyl-4(5)-methylimidazole,
where some of the alkylimidazoles stated under (B) can be replaced by 2-ethylimidazole, 4-methylimidazole, 2,4-dimethylimidazole and/or 2-methyl-4-ethylimidazole.

The present invention furthermore relates to a process for the preparation of the novel epoxy resin hardener, wherein either pure 2-ethyl-4-methylimidazole (A) is combined with the alkylimidazoles stated under (B), or the products formed in the dehydrogenation of 2-ethyl-4-methylimidazoline at from 400° to 550° C. over a catalyst containing zinc oxide are isolated by distillation of the reaction mixture, the fraction distilling between 250° and 274° C. under 1013 mbar preferably being isolated.

The novel epoxy resin hardeners remain liquid at room temperature and down to the freezing point of water, and therefore possess fairly advantageous processing and curing properties which are equivalent to, or better than, those of 2-ethyl-4-methylimidazole.

The epoxy resin hardener according to the invention comprises a mixture of
(A) from 65 to 95, preferably from 70 to 90, % by weight of 2-ethyl-4-methylimidazole and
(B) from 5 to 35, preferably from 8 to 20, % by weight of one or more compounds from the group consisting of 2-ethyl-4,5-dimethylimidazole and 2,5(4)-diethyl-4(5)-methylimidazole,
and some, eg. as much as 10% by weight, based on 2-ethyl-4-methylimidazole, of the alkylimidazoles stated under (B) can be replaced by 2-ethylimidazole, 4-methylimidazole, 2,4-dimethylimidazole or 2-methyl-4-ethylimidazole or a mixture of these. The sum of the percentages stated under (A) and (B) is 100.

The individual components of the mixture (B) can be present in various amounts, for example in amounts of from 0.5 to 20% by weight, based on the mixture of (A) and (B).

Mixtures of this type can contain, for example,
from 75 to 90% by weight of 2-ethyl-4-methylimidazole,
from 1 to 6% by weight of 2-ethylimidazole,
from 2 to 4% by weight of 4-methylimidazole,
from 0.5 to 1.5% by weight of 2,4-dimethylimidazole,
from 0.5 to 1.5% by weight of 2-methyl-4-ethylimidazole,
from 1 to 10% by weight of 2-ethyl-4,5-dimethylimidazole and
from 1 to 10% by weight of 2,5-diethyl-4-methylimidazole or 2,4-diethyl-5-methylimidazole.

The liquid epoxy resin hardeners according to the invention can be prepared by mixing the individual pure compounds stated under (A) and (B), or mixtures of these compounds.

Particularly advantageously, the mixtures according to the invention can be obtained by distillation of the products formed in the dehydrogenation of 2-ethyl-4-methylimidazoline at above 400° C., preferably from 400° to 550° C., over a catalyst containing zinc oxide.

The novel mixture is a viscous material at room temperature, and this material does not crystallize even after it is seeded with crystals and stored for a relatively long time in a refrigerator at from 0° to 5° C.

The dehydrogenation of 2-ethyl-4-methylimidazoline can be carried out as described in EP No. 0 000 208. By increasing the dehydrogenation temperature to 400°–500° C., the amounts of 2-alkyl-, 4-alkyl- and 2,4,5-trialkylimidazoles can be increased. The reaction mixture as obtained from the dehydrogenation can be distilled using a distillation apparatus containing only a single theoretical plate (Claisen head). Preferably, the distillation is carried out under atmospheric pressure and the fraction distilling at 250°–274° C./1013 mbar is recovered. However, distillation can also be carried out under reduced pressure. A typical composition of a hardener system which is liquid at room temperature comprises, for example,
85% of 2-ethyl-4-methylimidazole,
2.5% of 2-ethylimidazole,
1.5% of 4-methylimidazole,
0.5% of 2,4-dimethylimidazole,
0.5% of 2-methyl-4-ethylimidazole,
6% of 2-ethyl-4,5-dimethylimidazole and 4% of 2,5(4)-diethyl-4(5)-methylimidazole.

The novel liquid epoxy resin hardeners can be processed very advantageously and can be used together with the conventional epoxy resins. The ratio of epoxy resin to epoxy resin hardener according to the invention can vary within a wide range. The epoxy resin hardener can be used in an amount of, for example, from 0.1 to 50, preferably from 5 to 30, % by weight, based on the epoxide compound.

Suitable epoxy resins are the conventional epoxide compounds which contain on average more than one epoxide group per molecule.

As is known, the epoxide compounds can be saturated or unsaturated, aliphatic, cycloaliphatic, aromatic or heterocyclic and can possess substituents which do not take part in the reaction, eg. halogen atoms, hydroxyl groups, ether radicals and the like.

Preferred epoxide compounds are glycidyl ethers of polyhydric phenols, such as diphenylolalkanes, eg. diphenylolpropane, diphenylolethane and diphenylolmethane, diphenylol sulfone, hydroquinone, resorcinol, dihydroxydiphenyl and dihydroxynaphthalene, or polyhydric phenols, such as novolaks and resols, which are prepared by condensation of phenol and formaldehyde. The most suitable compounds are glycidyl polyethers of 2,2-bis-(4-hydroxyphenyl)-propane having a molecular weight of from 340 to 4,000.

Other useful epoxide compounds are polyepoxyalkyl ethers of aliphatic polyhydroxy compounds, eg. ethylene glycol, glycerol, trimethylolpropane and pentaerythritol, polyepoxyalkyl esters of polybasic carboxylic acids, for example the diglycidyl esters of phthalic acid, terephthalic acid and adipic acid, and polyglycidyl esters of polymeric unsaturated fatty acids, for example the diglycidyl ester of dimerized linoleic acid; epoxidized linseed oil or soybean oil; epoxidized dienes, such as diepoxybutane, and epoxidized vinylcyclohexane; diepoxyalkyl ethers in which two epoxyalkyl groups are bonded to a single oxygen atom, eg. diglycidyl ether; and polyepoxy compounds which are obtained by epoxidation of cyclohexane derivatives, eg. (3,4-epoxy-6-methylcyclohexyl)-methyl 3,4-epoxy-6-methylcyclohexanecarboxylate.

The novel epoxy resin hardeners can also be used in a conventional manner together with other reactants, eg. phenols, mercaptans, triphenylphosphine, triphenylarsine, triphenylstibine, amines, amine salts and quaternary ammonium salts, which are conventionally employed for the formation of epoxide polyadducts.

Examples of suitable amines which are conventionally used for the stated purpose and which can be employed together with the novel epoxy resin hardeners are benzyldimethylamine, dicyanodiamide, p,p'-bis-(dimethylaminophenyl)-methane, dimethylethanolamine, morpholine, dimethylaminopropylamine, m-phenylenediamine, polyalkylenepolyamines, such as diethylenetriamine, and mixtures of the above amines. The salts of these amines can be produced from an inorganic or organic acid and an amine, examples being the hydrochlorides, the sulfates and the acetates of the tertiary amines described above. Examples of quaternary compounds are benzyltrimethylammonium chloride, phenyltributylammonium chloride, cyclohexyltributylammonium sulfate, benzyltrimethylammonium sulfate, benzyltrimethylammonium borate, diphenyldioctylammonium chloride and mixtures of these.

These additional amines can be used in a conventional manner, in amounts of from 0.1 to 25, preferably from 1 to 5, % by weight, based on the epoxide compounds.

After the epoxide compound has been mixed with the epoxy resin hardener, the reaction is completed by heating the mixture obtained. Various additives, such as solvents, diluents, pigments, fillers, fibrous products, dyes, resins, plasticizers and non-volatile extenders can be added to the mixture before the reaction. If the epoxide compound is a relatively viscous liquid or a solid substance, the components can be heated as early as the mixing stage, or a solvent, eg. benzene, toluene, cyclohexane, a ketone, an ether, an ester or a nitrile, can be used.

Furthermore, monoepoxy diluents, such as butyl glycidyl ether, phenyl glycidyl ether and monoglycidyl esters can be used in a conventional manner. Monoepoxy diluents participate in the reaction, and can be used in an amount of, in general, not more than 20% by weight, based on the epoxide compound. It is also possible to use inert non-volatile extenders, such as coal tars, coal-tar pitches, asphalts, pine pitch, terpentine oil, lubricating oil fractions and their aromatic extracts, and lubricating oil raffinates.

The temperature employed during the reaction can vary within a wide range and is in general from about 40° to 300° C., preferably from 50° to 250° C.

The shaped articles obtained using the novel epoxy resin hardeners possess surprisingly high heat distortion resistance and have very good strength properties even at elevated temperatures. Moreover, they are very resistant to boiling water, powerful solvents and other chemicals, so that they are particularly useful for bonding and for the production of laminated materials and other moldings, for example for encapsulating electrical equipment, and may be useful as coatings. The novel epoxy resin hardeners are also suitable as cocatalysts in combination with amines, in particular for coating heat-resistant materials, such as glass fibers or carbon fibers, with epoxy resins.

Another advantage of the novel hardeners is that the compositions prepared with them can be brought to reaction at moderately elevated temperatures, so that when they are used there is no danger of adverse effects on the heat-sensitive material to which they are applied.

In the Examples which follows, parts and percentages are by weight, unless stated otherwise.

EXAMPLE 1

100 parts/hour of 2-ethyl-4-methylimidazoline are prevaporized in an electrically heated quartz vaporizer and diluted with 5,000 parts of nitrogen, and this mixture is then dehydrogenated, at 400° C., in a fluidized bed reactor which contains 200 parts of a dehydrogenation catalyst consisting of $ZnO/Al_2O_3$ (as described in more detail in EP No. 0 000 208). The mixture emerging from the reactor is distilled under atmospheric or reduced pressure in a distillation apparatus, without the use of a distillation column. 92 parts of an imidazole mixture are obtained per 100 parts of 2-ethyl-4-methylimidazoline used. This mixture contains, according to gas chromatographic analysis,
88.6% of 2-ethyl-4-methylimidazole,
1.4% of 2-ethylimidazole,
2.0% of 4-methylimidazole,
2.0% of 2-ethyl-4,5-dimethylimidazole,
5.0% of 2,5(4)-diethyl-4(5)-methylimidazole,
0.5% of 2,4-dimethylimidazole and 0.5% of 2-methyl-4-ethylimidazole,
and boils at 250°–274° C.

5 parts of unconverted 2-ethyl-4-methylimidazoline are separated off as light ends and recycled to the process. 3 parts of a black material remin as the distillation residue. The distillate is a viscous liquid which does not crystallize even after storage for more than 30 days in a refrigerator and daily rubbing with a glass rod.

EXAMPLE 2

If the procedure described in Example 1 is followed, except that a temperature of 500° C. is employed in the fluidized bed reactor, 89 parts of an imidazole mixture are obtained per 100 parts of 2-ethyl-4-methylimidazoline used. This mixture contains, according to gas chromatographic analysis,
78.5% of 2-ethyl-4-methylimidazole,
3.5% of 2-ethylimidazole,
3.5% of 4-methylimidazole,
9% of 2-ethyl-4,5-dimethylimidazole,
3.5% of 2,5(4)-diethyl-4(5)-methylimidazole,
1% of 2,4-dimethylimidazole and
1% of 2-methyl-4-ethylimidazole,
and boils at 160°–180° C. under 20–25 mbar.

3 parts of unconverted 2-ethyl-4-methylimidazoline are recovered as light ends. 8 parts of a black material remain as the distillation residue. The distillate remains liquid even after standing in a refrigerator for more than 30 days.

COMPARATIVE EXAMPLE 8.5 parts of 99.9% pure 2-ethyl-4-methylimidazole,
0.5 part of 2-ethyl-4-methylimidazoline,
0.5 part of 1-methylimidazole and
0.5 part of 4-methylimidazole
are melted together, and the melt is kept in a refrigerator. After standing for two days, the mixture begins to crystallize, and after a further two days it has crystallized completely.

We claim:
1. A liquid epoxy resin hardener which comprises a mixture of the following alkylimidazoles: (A) from 65 to 95% by weight of 2-ethyl-4-methylimidazole and (B) from 5 to 35% by weight of one or more compounds from the group consisting of 2-ethyl-4,5-dimethylimidazole and 2,5(4)-diethyl-4(5)-methylimidazole, where some of the alkylimidazoles stated under (B) can be replaced by 2-ethylimidazole, 4-methylimidazole, 2,4-dimethylimidazole or 2-methyl-4-ethylimidazole or by a mixture of two or more compounds from the group consisting of 2-ethylimidazole, 4-methylimidazole, 2,4-dimethylimidazole and 2-methyl-4-ethylimidazole.

2. A process for the preparation of the liquid epoxy resin hardener of claim 1, which comprises mixing pure 2-ethyl-4-methylimidazole (A) with the alkylimidazoles stated under (B).

3. A process for the preparation of the liquid epoxy resin hardener of claim 1, which comprises the distillation of the products formed in the dehydrogenation of 2-ethyl-4-methylimidazoline at from 400° to 550° C. over a catalyst containing zinc oxide and recovery of the distillate.

4. The process of claim 3, wherein the fraction distilling between 250° and 274° C. under 1013 mbar is recovered as the epoxy resin hardener.

* * * * *